(12) United States Patent
Han et al.

(10) Patent No.: US 10,349,944 B2
(45) Date of Patent: Jul. 16, 2019

(54) STENT FOR CONNECTING ADJACENT TISSUES AND MANUFACTURING METHOD THEREOF

(71) Applicant: M.I.TECH CO., LTD., Pyeongtaek-si, Gyeonggi-do (KR)

(72) Inventors: Jong Hyeon Han, Seoul (KR); Hun Kuk Park, Pyeongtaek-si (KR); Ho Yun, Asan-si (KR); Jong Pil Moon, Gunpo-si (KR); Bong Seok Jang, Osan-si (KR)

(73) Assignee: M.I. TECH CO., LTD., Pyeongtaek-si (KR)

( * ) Notice: Subject to any disclaimer, the term of this patent is extended or adjusted under 35 U.S.C. 154(b) by 144 days.

(21) Appl. No.: 15/301,168

(22) PCT Filed: May 12, 2015

(86) PCT No.: PCT/KR2015/004718
§ 371 (c)(1),
(2) Date: Sep. 30, 2016

(87) PCT Pub. No.: WO2016/125951
PCT Pub. Date: Aug. 11, 2016

(65) Prior Publication Data
US 2017/0014133 A1    Jan. 19, 2017

(30) Foreign Application Priority Data
Feb. 4, 2015  (KR) .................. 10-2015-0017323

(51) Int. Cl.
*A61B 17/11*    (2006.01)
*A61F 2/88*    (2006.01)
(Continued)

(52) U.S. Cl.
CPC .............. *A61B 17/11* (2013.01); *A61F 2/885* (2013.01); *A61F 2/90* (2013.01);
(Continued)

(58) Field of Classification Search
CPC .............. A61F 2/90; A61F 2/885; A61B 17/11
See application file for complete search history.

(56) References Cited

U.S. PATENT DOCUMENTS

| 6,620,122 B2 | 9/2003 | Stinson et al. ................... 604/8 |
| 9,320,624 B2 | 4/2016 | Shin |

(Continued)

FOREIGN PATENT DOCUMENTS

| CN | 1358482 A | 7/2002 |
| JP | 2006-506201 A | 2/2006 |

(Continued)

OTHER PUBLICATIONS

International Search Report dated Sep. 25, 2016, issued to International Application No. PCT/KR2015/004718.
(Continued)

*Primary Examiner* — Tuan V Nguyen
(74) *Attorney, Agent, or Firm* — Stein IP, LLC

(57) ABSTRACT

The present invention relates to a connection stent and a method of manufacturing the stent. The connection stent includes: a body configured to form a plurality of cells through the intersection of wires, and provided in a hollow cylindrical shape; an upper head formed to extend from one end of the body to have a diameter larger than that of the body; and a lower head formed to extend from a remaining end of the body to have a diameter larger than that of the body. The upper head and the lower head are respectively placed to come into contact with insides of heterogeneous tissues. Accordingly, according to the present invention, there can be manufactured a stent which can connect het- (Continued)

erogeneous tissues and form a bypass and which can provide sufficient expansion force and minimum axial force for the maintenance of the bypass formed as described above.

4 Claims, 18 Drawing Sheets

(51) Int. Cl.
*A61F 2/90* (2013.01)
*A61F 2/06* (2013.01)
*A61B 17/00* (2006.01)

(52) U.S. Cl.
CPC ............... *A61B 2017/00526* (2013.01); *A61B 2017/1139* (2013.01); *A61F 2/064* (2013.01); *A61F 2230/001* (2013.01); *A61F 2230/0065* (2013.01); *A61F 2240/002* (2013.01); *A61F 2240/005* (2013.01)

(56) References Cited

U.S. PATENT DOCUMENTS

| | | | |
|---|---|---|---|
| 9,535,590 B2 | 1/2017 | Danton et al. | |
| 2007/0179590 A1* | 8/2007 | Lu .......................... | A61F 2/07 623/1.16 |
| 2009/0082803 A1 | 3/2009 | Adams et al. ............... | 606/213 |
| 2009/0281557 A1* | 11/2009 | Sander .................. | A61B 17/11 606/151 |
| 2013/0310833 A1* | 11/2013 | Brown ............... | A61B 17/3476 606/45 |
| 2014/0303710 A1 | 10/2014 | Zhang et al. ................ | 623/1.11 |

FOREIGN PATENT DOCUMENTS

| | | |
|---|---|---|
| JP | 2011-519709 A | 7/2011 |
| JP | 2014-512195 A | 5/2014 |
| KR | 10-1076721 B1 | 10/2011 |
| KR | 10-2013-0106115 A | 9/2013 |
| KR | 10-2013-0110413 A | 10/2013 |
| KR | 10-2013-0126641 A | 11/2013 |
| WO | WO 2011/059190 A2 | 5/2011 |

OTHER PUBLICATIONS

U.S. Appl. No. 13/003,277, filed Dec. 6, 2012, Tieu.
Michel Kahaleh et al., "A Kit for EUS-Guided Access and Drainage of Pancreatic Pseudocysts: Efficacy in a Porcine Model", Nov. 2012.
Japanese Office Action dated Aug. 29, 2017, issued by the Japanese Patent Office in corresponding application JP 201580018516.1.
Japanese Office Action dated Aug. 1, 2016, issued by the Japanese Patent Office in corresponding application JP 2016-554717.
Korean Office Action dated Aug. 21, 2016, issued by the Korean Intellectual Property Office in corresponding application KR 10-2015-0017323.
European Search Report dated Jul. 19, 2018, issued to European Application No. 15881269.3.

* cited by examiner

STENT FOR CONNECTING ADJACENT TISSUES AND MANUFACTURING METHOD THEREOF

CROSS-REFERENCE TO RELATED APPLICATIONS

This application is a national stage of International Application No. PCT/KR2015/004718, filed May 12, 2015, which claims the benefit of priority to Korean Application No. 10-2015-0017323, filed Feb. 4, 2015, in the Korean Intellectual Property Office, the disclosures of which is incorporated herein by reference.

TECHNICAL FIELD

The present invention relates to a stent that forms a bypass by connecting heterogeneous tissues, and a method of manufacturing the stent.

BACKGROUND ART

In general, stents are used for the purpose of expanding constricted regions. Stents are formed to be suitable for their purposes based on the sizes and characteristics of various types of organs and inner cavities, i.e., placement targets, and environments, and are provided to overcome the blocking or obstruction of the flow of materials attributable to the constriction of inner cavities and to ensure the sufficient diameters of inner cavities for a prolonged period.

Meanwhile, in addition to the purpose of expanding a constricted region, various purposes of stents have been recently proposed. That is, stents are used to guide various surgical instruments through their paths and to generate additional paths for surgical instruments, as well as to recover the diameters of material paths through expansion.

Preceding documents related to conventional technologies contrived to use a stent for a purpose, other than the purpose of expanding a constricted region, include Korean Patent Application Publication No. 10-2013-0110413 entitled "Stent for Anastomosis" (hereinafter referred to as a "conventional technology"). In this conventional technology, a separate connection path connecting heterogeneous organs is formed, the heterogeneous organs are inosculated together, and the inoculation is maintained.

However, the conventional technology is used for the purpose of anastomosis, and thus an inosculated state is maintained by bringing heterogeneous organs into tight contact with each other and flare parts extending from both ends of a body are formed to be spread at an obtuse angle. Accordingly, the conventional technology is problematic in that it is difficult to ensure and maintain the diameter of a path sufficient for the movement of surgical instruments, and in that it is also difficult to ensure sufficient separation prevention capability, and thus the stent is separated from a location where the stent is placed.

Furthermore, the conventional technology is problematic in that the intersections of the wires of the stent connecting heterogeneous organs are configured in the same structure, and thus the metallic fatigue of the wires increases in the process of ensuring and maintaining the diameter of a path for a surgical instrument, such as an endoscope, against external forces being exerted on the stent, thereby resulting in a reduction in the lifespan of the wires constituting the stent.

DISCLOSURE

Technical Problem

Accordingly, the present invention is intended to overcome the above-described problems, and an object of the present invention is to provide a connection stent that is formed by weaving two wires in a certain manner, thereby providing the diameter of a path sufficient for the movement of a surgical instrument, such as an endoscope, and ensuring the structural stability of the formed path, and also provide a technology capable of manufacturing the connection stent.

Technical Solution

In order to accomplish the above object, the present invention provides a connection stent, including: a body configured to form a plurality of cells through the intersection of wires, and provided in a hollow cylindrical shape; an upper head formed to extend from one end of the body to have a diameter larger than that of the body; and a lower head formed to extend from a remaining end of the body to have a diameter larger than that of the body; wherein the upper head and the lower head are respectively placed to come into contact with insides of heterogeneous tissues.

In this case, the upper head includes: a first portion bent and formed to extend from the one end of the body toward directions away from an outer circumference of the body; a second portion formed to extend from the first portion toward directions away from the one end of the body in a shape in which a diameter thereof is increased; and a third portion formed to extend from the second portion toward directions away from the one end of the body in a shape in which a diameter is decreased; and the lower head includes: a fourth portion bent and formed to extend from the remaining end of the body toward directions away from the outer circumference of the body; a fifth portion formed to extend from the fourth portion toward directions away from the remaining end of the body in a shape in which a diameter thereof is increased; and a sixth portion formed to extend from the fifth portion toward directions away from the remaining end of the body in a shape in which a diameter is decreased.

Furthermore, the first portion is bent from the one end of the body toward directions away from the outer circumference of the body at an angle ranging from 85° to 90° with respect to a central axis of the body; and the fourth portion is bent from the remaining end of the body toward directions away from the outer circumference of the body at an angle ranging from 85° to 90° with respect to the central axis of the body.

In this case, the first portion and the fourth portion are bent toward directions away from the outer circumference of the body at an identical angle with respect to the central axis of the body, and are provided so as to be opposite to each other.

Meanwhile, in order to accomplish the above object, the present invention provides a method of manufacturing a connection stent, the method being configured to form cells through intersection of at least one wire while moving the wires from a starting point, as which any one reference location point is set, upward and downward so that the wire passes over protruding pins located in diagonal directions by using a jig in which detachable protruding pins are installed at all respective location points at which circumference division lines and length division lines, formed by equally dividing a circumference (W) and length (L) of a cylinder having a diameter (R) identical to that of the body of the connection stent to be manufactured, intersect each other, the method including: step A of forming a part of a first body by bending and moving a first wire from a first starting point at one end of the jig to a first point at a remaining end of the jig in a zigzag form; step B of forming a lower first head by repeating a pattern of bending the first wire in a zigzag form from the first point to a first change point at the remaining end of the jig along a circumferential surface of a lower head formation member which is fitted around a one end-side circumferential surface of the jig to protrude and in which detachable protruding pins are installed at all location points corresponding the circumference division lines on a head length division line set along one side circumference; step C forming a part of the first body by bending and moving the first wire from the first change point to a second point at the one end of the jig in a zigzag form; and step D of forming an upper first head by repeating a pattern of bending the first wire in a zigzag form from the second point to the first staring point along a circumferential surface of an upper head formation member which is fitted around an remaining end-side circumferential surface of the jig to protrude and be opposite to the lower head formation member and in which detachable protruding pins are installed at all location points corresponding the circumference division lines on a head length division line set along one side circumference.

In this case, step A includes: step A-1 of repeating a zigzag bent pattern formed by moving the first wire from the first starting point along an upward diagonal line by l (a distance of the diagonal line extending by one interval between the length division lines for one interval between the circumference division lines) and then moving the first wire from that location point along a downward diagonal line by l; and step A-2 of spacing a location point from the portion formed at step A-1 by moving the first wire from the end point of step A-1 along a downward diagonal line by 2l; step C includes: step C-1 of repeating a zigzag bent pattern formed by moving the first wire from the first change point along a downward diagonal line by l and then moving the first wire from that location point along an upward diagonal line by l; and step C-2 of spacing a location point from the portion formed at step C-1 by moving the first wire from the end point of step C-1 along an upward diagonal line by 2l; and step A alternately performs step A-1 and step A-2, and step C alternately performs step C-1 and step C-2.

The first point is located on the same length division line as the first change point, is also located on the same circumference division line as an even-numbered end point of a plurality of end points of step A-1, and corresponds to a last end point of the plurality of end points of step A-1 formed in a process in which step A-1 and step A-2 are alternately performed.

Furthermore, the second point is located on the same length division line as the first starting point, is also located on the same circumference division line as an even-numbered end point of a plurality of end points of step C-1, and corresponds to a last end point of the plurality of end points of step C-1 formed in a process in which step C-1 and step C-2 are alternately performed.

Step B includes: step B-1 of bending the first wire at a first bending point, reached by moving the first wire from the first point along a downward diagonal line of tangent lines, which the lower head formation member forms with the jig, by l (a distance of a diagonal line extending by one interval between the length division lines for one interval between the circumference division lines), to come into contact with a lower bent portion forming a ring-shaped bottom surface of the lower head formation member; step B-2 of repeating a zigzag bent pattern formed by moving the first wire bent from the first bending point of step B-1 along a downward diagonal line l' (a distance over which movement is performed from the first bending point to a location point, which corresponds to a circumference division line corresponding to a location that is shifted by three intervals based on a circumference division line of the first bending point, among location points on a head length division line set within the lower head formation member) along a circumferential surface of a lower curved portion formed to extend in a shape in which a diameter of the lower curved portion is increased from the lower bent portion of the lower head formation member and is then decreased and then moving the first wire from that location point along an upward diagonal line l' along the circumferential surface of the lower curved portion, thereby returning to the first bending point; and step B-3 of bending the first wire at the first bending point, reached again via step B-2, to come into contact with the circumferential surface of the jig, and then locating the first wire at the first change point by moving the first wire from the first bending point along an upward diagonal line by l.

Furthermore, step D includes: step D-1 of bending the first wire at a second bending point, reached by moving the first wire from the second point along a upward diagonal line of tangent lines, which the upper head formation member forms with the jig, by l (a distance of a diagonal line extending by one interval between the length division lines for one interval between the circumference division lines), to come into contact with an upper bent portion forming a ring-shaped bottom surface of the upper head formation member; step D-2 of repeating a zigzag bent pattern formed by moving the first wire bent from the second bending point of step D-1 along an upward diagonal line by l' (a distance over which movement is performed from the second bending point to the location point, which corresponds to a circumference division line corresponding to a location that is shifted by three intervals based on the circumference division line of the second bending point, among location points on the head length division line set within the upper head formation member) along a circumferential surface of an upper curved portion formed to extend in a shape in which a diameter of the upper curved portion is increased from the upper bent portion of the upper head formation member and is then decreased, and then moving the first wire from that location point along an upward diagonal line by l' along the circumferential surface of the upper curved portion, thereby returning to the second bending point; and step D-3 of bending the first wire at the second bending point, reached again via step D-2, to come into contact with the circumferential surface of the jig and then locating the first wire at the first starting point by moving the first wire from the second bending point along a downward diagonal line by l.

Furthermore, the method further includes: step E of forming a part of a second body by bending and moving a second wire in a zigzag form from a second starting point at the one end of the jig to a third point at the remaining end of the jig; step F of forming a lower second head by repeating a pattern of bending the second wire in a zigzag form from the third point to the second change point at the remaining end of the jig along the circumferential surface of the lower head formation member; step G of forming a part of the second body by bending and moving the second wire from the second change point to a fourth point at the one end of the jig in a zigzag form; and step H of forming an upper second head by repeating a pattern of bending the second wire in a zigzag form from the fourth point to the second starting point along the circumferential surface of the upper head formation member; and the second starting point is located so as to be spaced apart by a predetermined interval based on the circumference division lines, on an identical length division line on which the first starting point is located.

In this case, the second starting point corresponds to a location, which is shifted in a circumferential direction by an odd number of circumference division lines, on the identical length division line on which the first starting point is located.

Furthermore, step E includes: step E-1 of repeating a zigzag bent pattern formed by moving the second wire from the second starting point along an upward diagonal line by l (a distance of the diagonal line extending by one interval between the length division lines for one interval between the circumference division lines) and then moving the second wire from the location point along a downward diagonal line by l; and step E-2 of spacing a location point from a portion formed at step E-1 by moving the second wire from the end point of step E-1 along a downward diagonal line by 2l; step G includes: step G-1 of repeating a zigzag bent pattern formed by moving the second wire from the second change point along a downward diagonal line by l and then moving the second wire from that location point along an upward diagonal line by l; and step G-2 of spacing a location point from the portion formed at step G-1 by moving the second wire from the end point of step G-1 along an upward diagonal line by 2l; and step E alternately performs step E-1 and step E-2, and step G alternately performs step G-1 and step G-2.

In this case, the third point is located on the same length division line as the second change point, is also located on the same circumference division line as an even-numbered end point of a plurality of end points of step E-1, and corresponds to a last end point of the plurality of end points of step E-1 formed in a process in which step E-1 and step E-2 are alternately performed.

Furthermore, the fourth point is located on the same length division line as the second starting point, is also located on the same circumference division line as an even-numbered end point of a plurality of end points of step G-1, and corresponds to a last end point of the plurality of end points of step G-1 formed in a process in which step G-1 and step G-2 are alternately performed.

Furthermore, step F includes: step F-1 of bending the second wire at a third bending point, reached by moving the second wire from the third point along a downward diagonal line of tangent lines, which the upper head formation member forms with the jig, by l (a distance of a diagonal line extending by one interval between the length division lines for one interval between the circumference division lines), to come into contact with the lower bent portion; step F-2 of repeating a zigzag bent pattern formed by moving the second wire bent from the third bending point of step F-1 along a downward diagonal line by l' (a distance over which movement is performed from the third bending point to a location point, which corresponds to a circumference division line corresponding to a location that is shifted by three intervals based on a circumference division line of the third bending point, among location points on a head length division line set within the lower head formation member) along the circumferential surface of the lower curved portion and then moving the second wire from that location point along an upward diagonal line by l' along the circumferential surface of the lower curved portion, thereby returning to the third bending point; and step F-3 of bending the second wire at the third bending point, reached again via step F-2, to come into contact with the circumferential surface of the jig, and then locating the second wire at the second change point by moving the second wire from the third bending point along an upward diagonal line by l.

Moreover, step H includes: step H-1 of bending the second wire at a fourth bending point, reached by moving the second wire from the fourth point along a upward diagonal line of tangent lines, which the upper head formation member forms with the jig, by l (a distance of a diagonal line extending by one interval between the length division lines for one interval between the circumference division lines), to come into contact with the upper bent portion; step H-2 of repeating a zigzag bent pattern formed by moving the second wire bent from the fourth bending point of step H-1 along an upward diagonal line by l' (a distance over which movement is performed from the fourth bending point to the location point, which corresponds to a circumference division line corresponding to a location that is shifted by three intervals based on the circumference division line of the fourth bending point, among location points on the head length division line set within the upper head formation member) along the circumferential surface of the upper curved portion and then moving the second wire from that location point along a downward diagonal line by l' along the circumferential surface of the upper curved portion, thereby returning to the fourth bending point; and step H-3 of bending the second wire at the fourth bending point, reached again via step H-2, to come into contact with the circumferential surface of the jig and then locating the second wire at the second starting point by moving the second wire from the fourth bending point along an downward diagonal line by l.

Advantageous Effects

The stent manufactured according to the present invention and configured to connect heterogeneous tissues has the following effects:

First, the stent can form a separate bypass that is intended to shorten a path for an instrument, such as an endoscope, which is inserted into a human body to perform surgery, and to increase accessibility between the heterogeneous tissues.

Second, various types of materials in a human body, such as body fluids, can be easily discharged via the bypass formed as described above.

Third, the woven structure of wires constituting the body of the stent is formed to have an axial force close to 0 and a high-level radial force, and thus the stent can maintain an expanded state for a prolonged period after placement, thereby providing desirable durability of the bypass that connects heterogeneous tissues.

Fourth, the heads at the ends of the body are bent and extend from the body at approximately right angles, and thus are placed in contact with inner sides of heterogeneous tissues, thereby enhancing separation prevention capability.

Fifth, the shape of intersection of the wires is configured to form a curved line in a direction toward the outer end of each of the heads, and thus areas of contact on the inside surfaces of tissues are reduced, thereby reducing damage to the tissues caused by the wires of both head portions.

MODE FOR INVENTION

Preferred embodiments of the present invention will be described in greater detail with reference to the accompanying drawings. Descriptions of well-known technical portions will be omitted or abridged for brevity of description.

1. Descriptions of Components and Operation of Connection Stent

Figure 1:
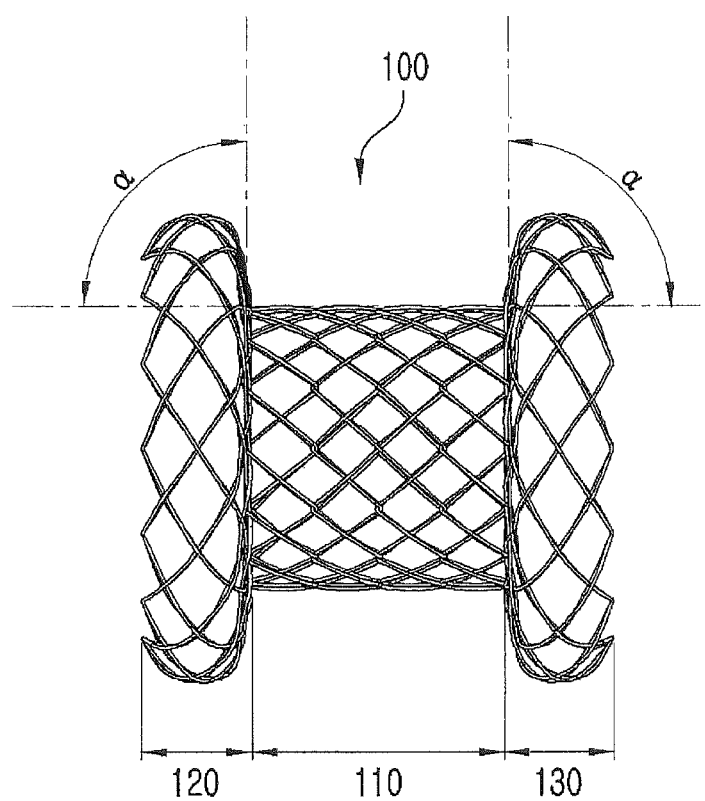
FIG. 1 is a plan view showing the structure of a connection stent according to the present invention.
Figure 2:
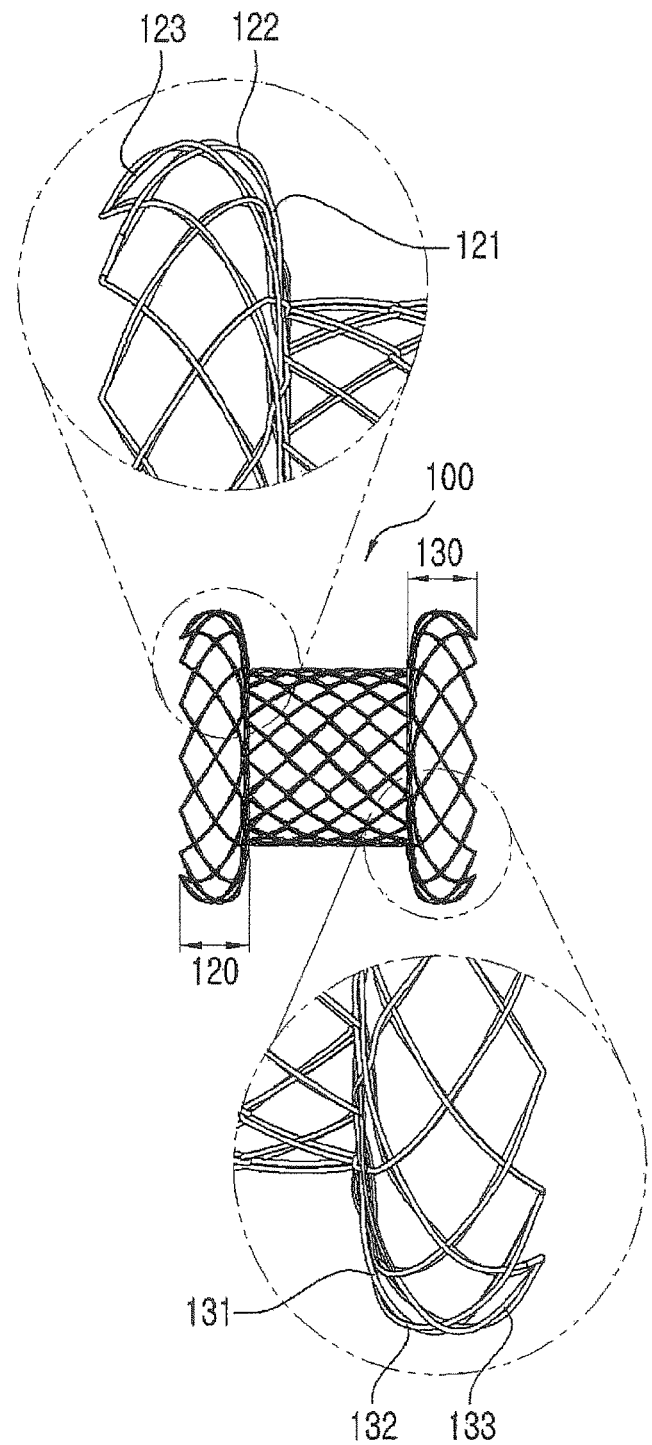
FIG. 2 is an enlarged view showing the structure of an upper head within the connection stent according to the present invention.
Figure 3:
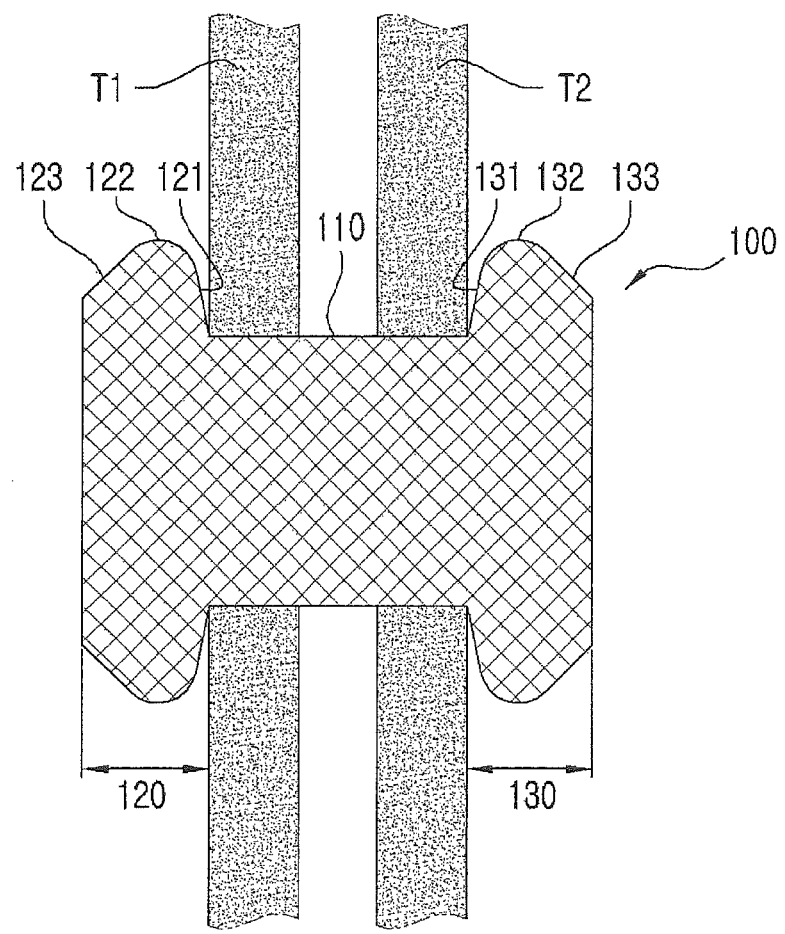
FIG. 3 shows the state in which the connection stent according to the present invention is placed.
Figure 4:
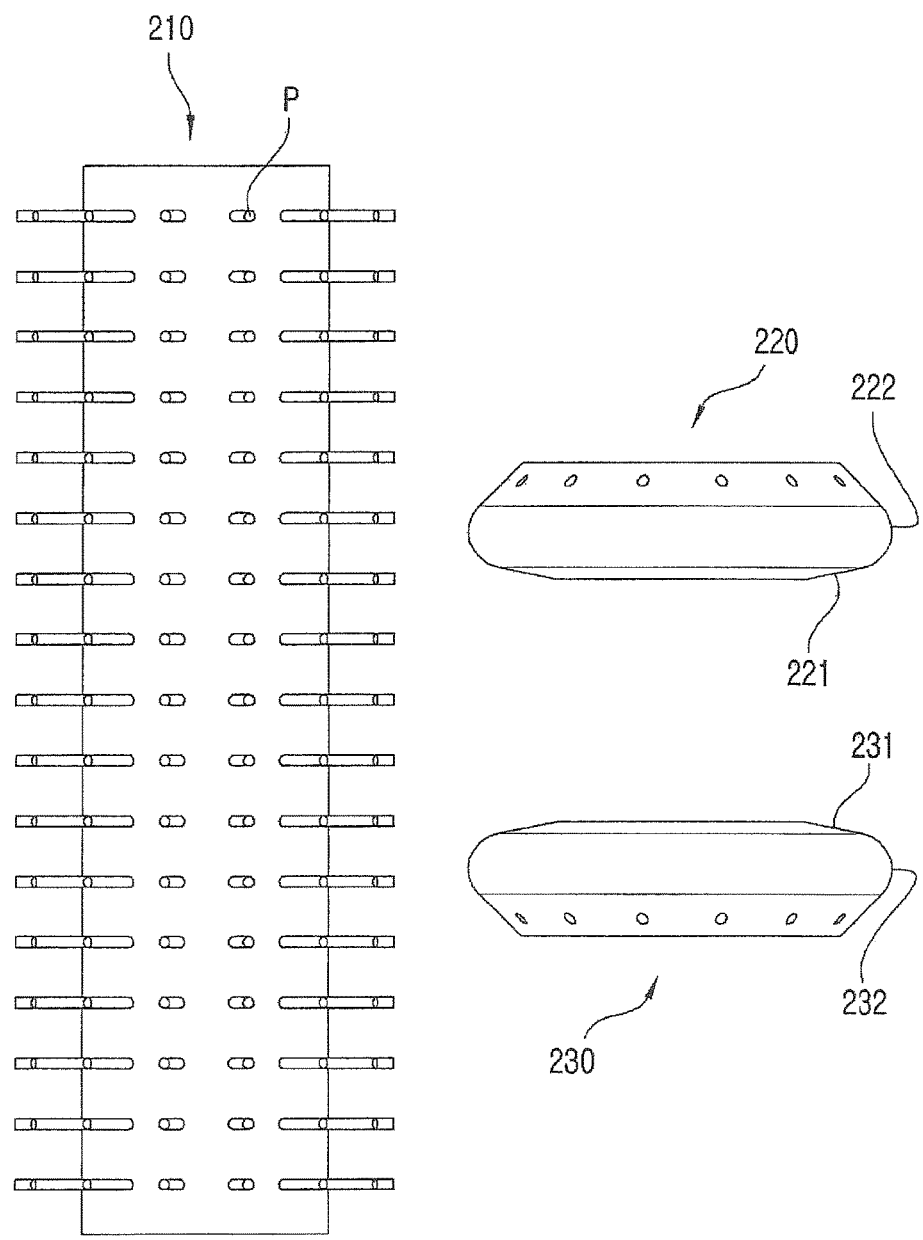
FIG. 4 is a front view showing the configuration of a connection stent manufacturing apparatus that is used for a method of manufacturing a connection stent according to the present invention.

Referring to FIGS. 1 to 3, a connection stent 100 according to the present invention includes a body 110; an upper head 120; and a lower head 130.

The body 110 has a plurality of cells formed through intersection of metallic wires, and is provided in a hollow cylindrical shape.

In this case, the shape of the body 110 and the structure of the plurality of cells, adapted to constitute the body 110 and formed to be opened through the intersection of wires, are not limited to specific shapes, but may be provided in various shapes.

The upper head 120 is formed to extend from one end of the body 110 to have a diameter larger than that of the body 110.

In this case, as shown in FIGS. 1 and 2, with regard to the shape of the upper head 120, the upper head 120 is outwardly bent and spread from the one end of the body 110, thereby forming a ring-shaped raised wall, and is formed to extend from the bent and spread portion toward directions away from the one end of the body 110 in a shape in which the diameter thereof is increased by a predetermined length and then in a shape in which the diameter thereof is decreased, thereby forming a curved shape.

In other words, more specifically, as shown in one enlarged portion of FIG. 2, the upper head 120 includes: a first portion 121 bent from the one end of the body 110 and formed to extend in directions away from the outer circumferential surface of the body 110; a second portion 122 formed to extend from the first portion 121 toward directions away from the one end of the body 110 in a shape in which the diameter thereof is increased; and a third portion 123 formed to extend from the second portion 122 toward directions away from the one end of the body 110 in a shape in which the diameter thereof is decreased.

In this case, the first portion 121 is bent from the one end of the body 110, and is bent and formed to extend while forming a predetermined angle α with the circumferential surface of the body 110, as shown in FIG. 2, thereby providing a ring-shaped surface that performs a function, such as that of a stop protrusion.

Furthermore, the first portion 121 is bent from the one end of the body 110 toward directions away from the outer circumferential surface of the body 110 at an angle ranging from 85° to 90° with respect to the central axis of the body 110. More specifically, the first portion 121 is preferably bent at a right angle.

Furthermore, the diameter of the third portion 123 that is decreased from the diameter of one end of the second portion 122 is preferably a diameter larger than that of the body 110 as a result.

The lower head 130 is formed to extend from the other end of the body 110 to have a diameter larger than that of the body 110.

In this case, as shown in FIGS. 1 and 2, with regard to the shape of the lower head 130, the lower head 130 is outwardly bent and spread from the other end of the body 110, thereby forming a ring-shaped raised wall, and is formed to extend from the bent and spread portion toward directions away from the other end of the body 110 in a shape in which the diameter thereof is increased by a predetermined length and then in a shape in which the diameter thereof is decreased, thereby forming a curved shape.

In other words, more specifically, as shown in another enlarged portion of FIG. 2, the lower head 130 includes: a fourth portion 131 bent from the other end of the body 110 and formed to extend in directions away from the outer circumferential surface of the body 110; a fifth portion 132 formed to extend from the fourth portion 131 toward directions away from the other end of the body 110 in a shape in which the diameter thereof is increased; and a sixth portion 133 formed to extend from the fifth portion 132 toward directions away from the other end of the body 110 in a shape in which the diameter thereof is decreased.

In this case, the fourth portion 131 is bent from the other end of the body 110, and is bent and formed to extend while forming a predetermined angle α with the circumferential surface of the body 110, as shown in FIG. 2, thereby providing a ring-shaped surface that performs a function, such as that of a stop protrusion.

Furthermore, the fourth portion 131 is bent from the other end of the body 110 toward directions away from the outer circumferential surface of the body 110 at an angle ranging from 85° to 90° with respective to the central axis of the body 110. More specifically, the fourth portion 131 is preferably bent at a right angle.

Additionally, as shown in FIG. 1, the fourth portion 131 is preferably provided in the shape of being bent toward directions away from the outer circumference of the body 110 at the same angle α as the first portion 121 of the upper head 120 based on the central axis of the body 110 and being opposite to the first portion 121 of the upper head 120.

Furthermore, the diameter of the sixth portion 133 that is decreased from the diameter of one end of the fifth portion 132 is preferably a diameter larger than that of the body 110 as a result.

Meanwhile, the upper head 120 and the lower head 130 formed on both end sides of the body 110 are placed to come into contact with insides of heterogeneous tissues.

That is, the connection stent 100 of the present invention is placed between heterogeneous tissues. The placement of the connection stent 100 is described in greater detail with reference to FIG. 3. That is, the upper head 120 is placed to come into contact with the inner wall T1 of a first tissue, while the lower head 130 is placed to come into contact with the inner wall T2 of a second tissue.

In this case, the body 110 is provided in the form of a hollow cylinder, and is used as a path that connects heterogeneous tissues. More specifically, the body 110 functions as a bypass for the movement of an endoscope.

In this case, an endoscope may be moved via the bypass and used to distribute various materials in a human body, such as body fluids in the second tissue. In order to facilitate the movement of such an endoscope, the diameter of the body 110 is preferably provided so as to be larger than that of the endoscope.

Additionally, the upper head 120 and the lower head 130 are provided in a shape in which the portions 122 and 123, and 132 and 133 that extend from the first portion 121 and the fourth portion 131, provided so as to be bent and formed to extend from both ends of the body 110, to directions away from both ends of the body 110 and complete the shapes of the heads are provided in a shape in which the diameter of the portions 122 and 132 is increased by a predetermined length and then the diameter of the portions 123 and 133 is decreased, thereby ensuring structural stability in the tissues in which the stent is placed.

In other words, the first portion 121 and the fourth portion 131, which are bent at and formed to extend from both ends of the body 110 toward directions away from the outer circumferential surface of the body 110 at an angle ranging from 85° to 90° with respect to the central axis of the body 110, impart stability and higher separation prevention capability to the connection stent 100 on the inner wall T1 of the first tissue and the inner wall T2 of the second tissue.

Furthermore, the longitudinal section-based curved and tapered shapes of the second and third portions 122 and 123 and the fifth and sixth portions 132 and 133, formed to extend from the first portion 121 and the fourth portion 131 toward directions away from both ends, reduce areas of contact with the inner wall T1 of the first tissue and the inner wall T2 of the second tissue, thereby minimizing damage to the tissues attributable to movement during or after the placement of the connection stent 100.

Furthermore, the connection stent 100 configured as described above may include a film which surrounds the inner surface or outer surface of the connection stent 100 and which has the shape of a hollow cylinder.

In this case, the material of the film may be selected from among polytetrafluoroethylene (PTFE), silicone, polyurethane, polyester, polypropylene, polyethylene, polyolefin, high density polyethylene (HDPE), and expanded-polytetrafluoroethylene (ePTFE), but may be selected from the range of well-known materials that are used for films without any limitation.

Furthermore, at least one radio-opaque marker (not shown) may be attached onto the wire circumferential surface of at least one of the body 110, the upper head 120 and the lower head 130 constituting the connection stent 100 in order to ensure the visibility of the connection stent 100 placed in a human body.

In this case, the radio-opaque marker (not shown) ensures visibility when the connection stent 100 is inserted into a human body via inspection using a radioactive ray, such as an X ray or the like, and thus the connection stent 100 can be accurately located in a desired region.

2. Descriptions of Method of Manufacturing Connection Stent

The process of a method of manufacturing a connection stent according to the present invention will be described in detail below with reference to the flowchart of FIG. 19 and the drawings of FIGS. 4 to 18.

First, FIGS. 6 to 15 show a structure formed by a first wire and a method of forming the structure, in the method of manufacturing the connection stent 100 by using a connection stent manufacturing apparatus 200 according to the practice of the present invention.

In this case, the dotted lines shown in the development views represent paths of a wire that has moved, and the solid lines represent paths of the wire that is moving at the corresponding step of each drawing.

Figure 5:
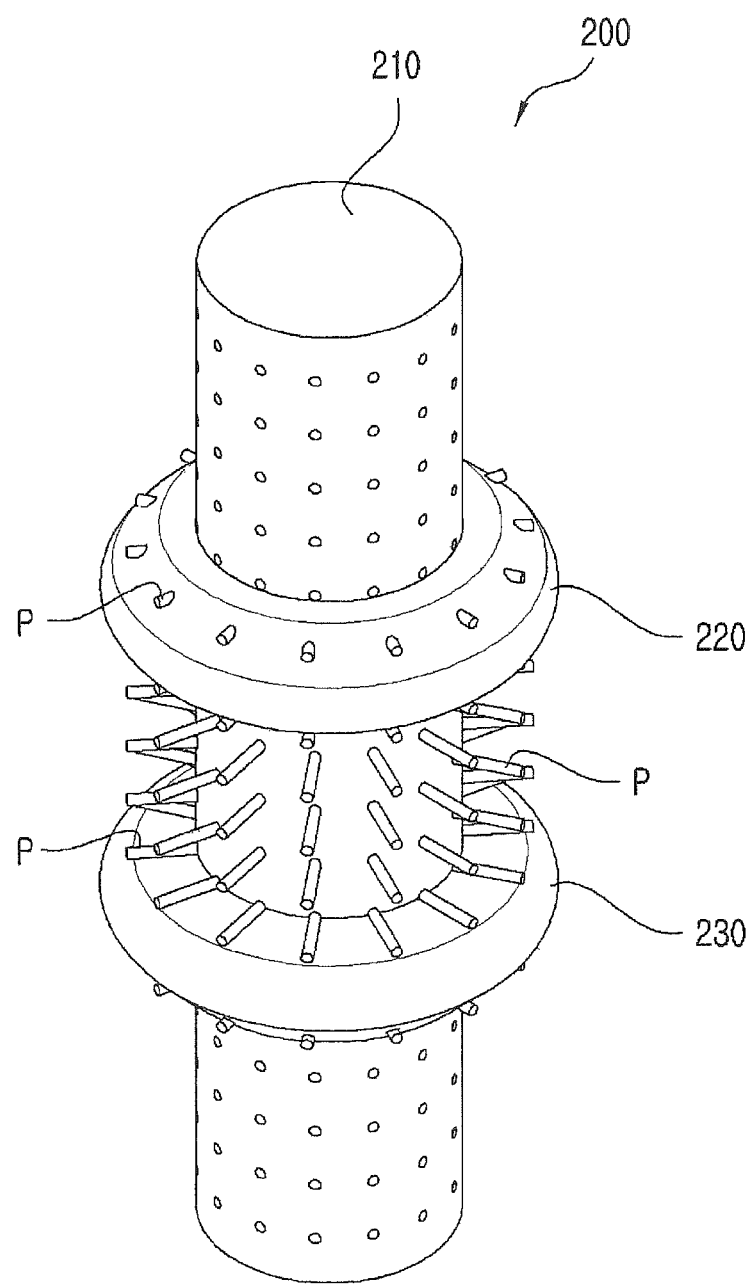
FIG. 5 is a perspective view showing the state in which the connection stent manufacturing apparatus that is used for a method of manufacturing a connection stent according to the present invention is assembled.

Additionally, the connection stent manufacturing apparatus 200, which is the basis for the manufacturing of the connection stent 100, is provided to include a jig 210, an upper head formation member 220, and a lower head formation member 230, as shown in FIG. 5.

In this case, in the jig 210, detachable protruding pins P may be installed at all respective location points at which circumference division lines $a_1, a_2, a_3, \ldots, a_{14}$ and length division lines $b_1, b_2, b_3, \ldots, b_{20}$, formed by respectively equally dividing the circumference W and length L of a cylinder having a diameter R identical to that of the body 110 of the connection stent 100 to be manufactured and also having a predetermined length L, intersect each other.

Furthermore, the upper head formation member 220 is a shaping mold that determines the shape of the upper head 120 formed to extend from one end of the body, and is fitted around the circumferential surface of one end side of the jig 210. Detachable protruding pins may be installed at all respective location points on a head length division line $h_1$ set along a circumference on one side, which correspond to the circumference division lines.

In this case, the upper head formation member 220 includes: an upper bent portion 221 configured to form a ring-shaped bottom surface that forms a predetermined angle with the circumferential surface of the jig 210, thereby providing a raised wall; and an upper curved portion 222 formed to extend from the upper bent portion 221 toward the direction of one end of the jig 210 in a ring shape in which the diameter is increased by a predetermined length and then in a shape in which the diameter is decreased.

In this case, the head length division line $h_1$ set along the circumference of one side of the upper head formation member 220 is preferably located on the upper curved portion 222.

Additionally, the lower head formation member 230 is a shaping mold that determines the shape of the lower head 130 formed to extend the other end of the body, and is fitted around the circumferential surface of the other end side of the jig 210 to be opposite to the upper head formation member 220. Detachable protruding pins may be installed at all respective location points on a head length division line $h_2$ set along a circumference on the other side, which correspond to the circumference division lines.

In this case, the lower head formation member 230 includes: a lower bent portion 231 configured to form a ring-shaped bottom surface that forms a predetermined angle with the circumferential surface of the jig 210, thereby providing a raised wall; and a lower curved portion 232 formed to extend from the lower bent portion 231 toward the direction of the other end of the jig 210 in a ring shape in which the diameter is increased by a predetermined length and then in a shape in which the diameter is decreased.

In this case, a head length division line $h_2$ set along the circumference of one side of the lower head formation member 230 is preferably located on the lower curved portion 232.

Using the connection stent manufacturing apparatus 200 including the jig 210, the upper head formation member 220 and the lower head formation member 230, the connection stent 100 is manufactured by setting any one of the location points as a starting point and repeatedly bending and moving the first wire 10 upward and downward so that the first wire 10 passes over the protruding pins P located in diagonal directions from the starting point to thus perform intersection and form cells.

(1) First Wire Lowering Step <S100>

Figure 6:
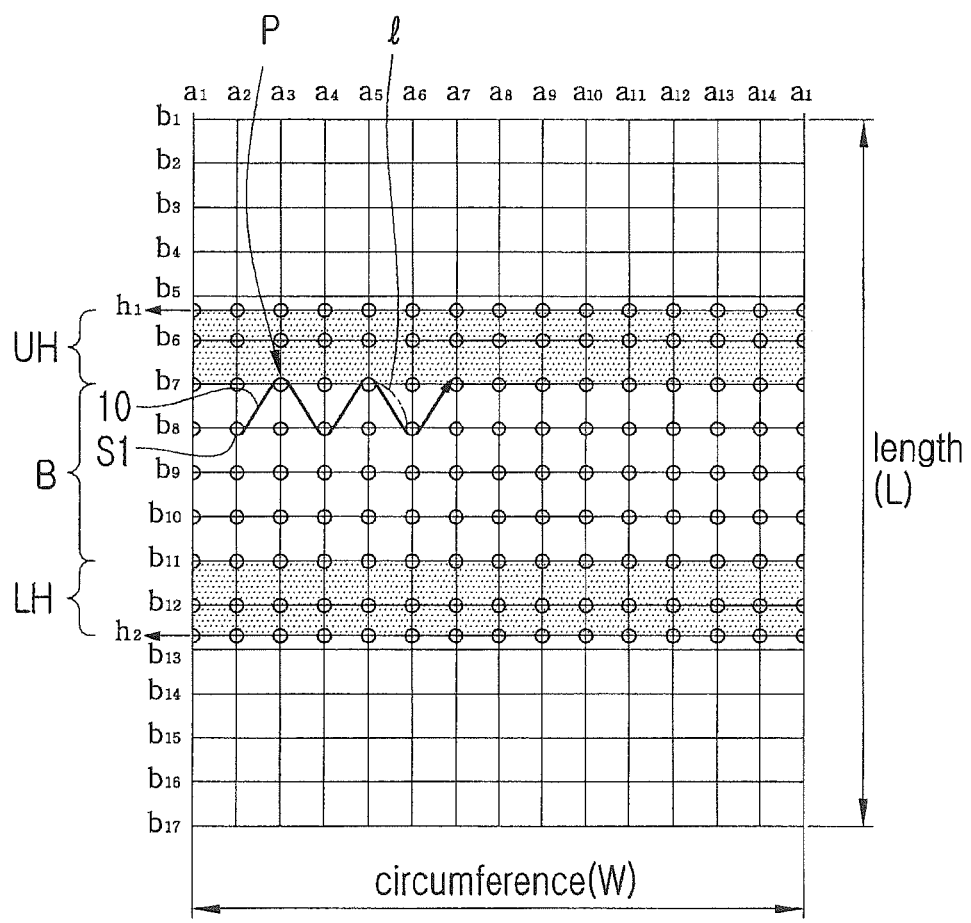
FIGS. 6 to 8 are development views illustrating a first wire lowering step according to the present invention.
Figure 7:
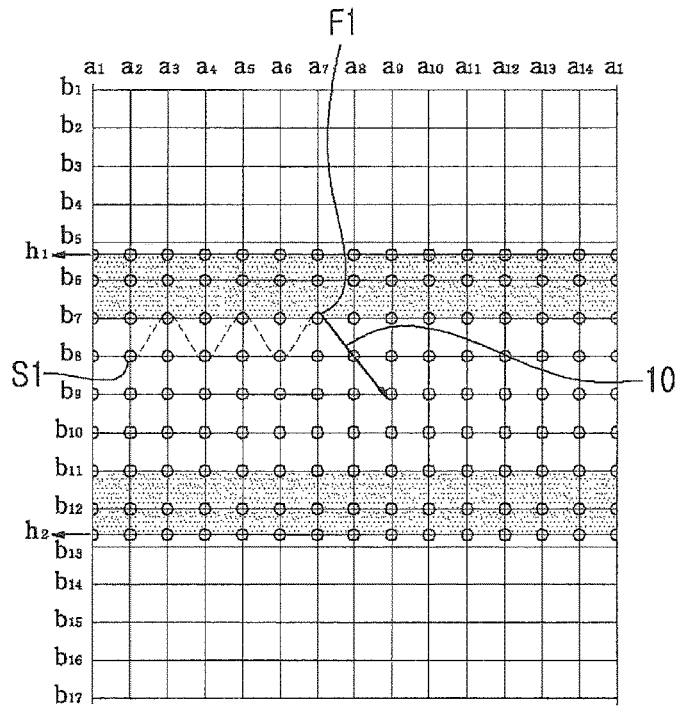
Figure 8:
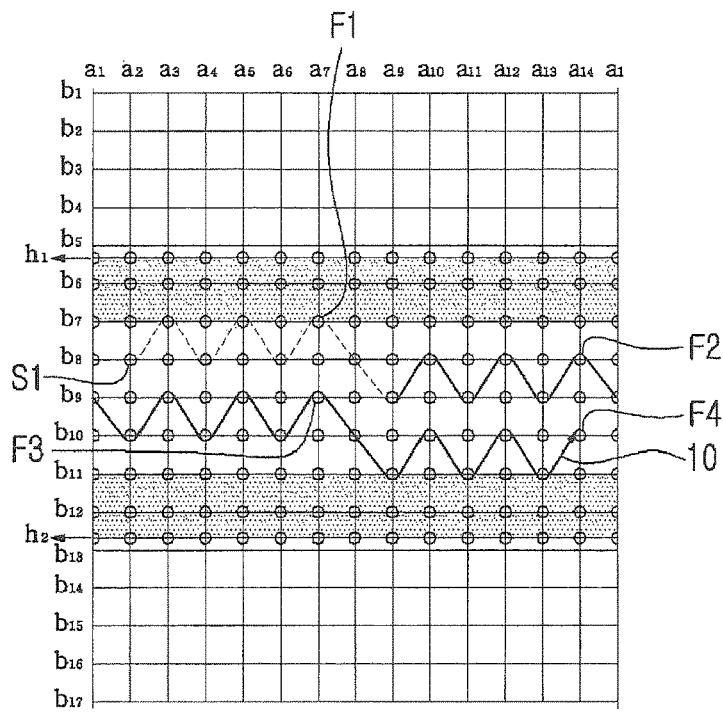

At the present step, as shown in FIGS. 6 to 8, the first wire 10 is bent and moved in a zigzag form from the starting point S1 ($a_2/b_8$) at one end of the jig to a first point F4 ($a_{14}/b_{10}$) at the other end of the jig. This process includes: a first zigzag movement step of repeating a zigzag bent pattern formed by moving the first wire 10 from the first starting point S1 along an upward diagonal line by l (the distance of the diagonal line extending by one interval between the length division lines for one interval between the circumference division lines) and then moving the first wire 10 from the location point $a_3/b_7$ along a downward diagonal line by l, as shown in FIG. 6; and a first spacing step of spacing a location point from a portion formed at the zigzag movement step by moving the first wire 10 from the end point F1 ($a_7/b_7$) of the first zigzag movement step along a downward diagonal line by 2l, as shown in FIG. 7.

The first zigzag movement step and the first spacing step are alternately performed. That is, the first zigzag movement step and the first spacing step continue to be performed, as shown in FIG. 8. The first wire lowering step S100 ends at the end point F4 ($a_{14}/b_{10}$) of a specific first zigzag movement step.

As a result, a first point, which is the last location point of the first wire lowering step S100 and which is the starting location point of a lower first head formation step S200, corresponds to a last end point F4 of many end points F1, F2, F3 and F4 formed in the process in which the first zigzag movement step and the first spacing step are alternately performed. The first end point F4 is located on the same length division line as a first change point C1 (a2/b10), and is located on the same circumference division line as an even-numbered end point F2 of many end points F1, F2, F3 and F4 formed in the process in which the first zigzag movement step and the first spacing step are alternately performed.

(2) Lower First Head Formation Step <S200>

At the present step, there is performed a lower first head formation step of forming a part of the lower head 130 by repeating a pattern of bending the first wire 10 in a zigzag form from the first point F4, located after the part of the stent body 110 has been formed during the lowering of the first wire 10 via step S100, to the first change point C1 ($a_2/b_{10}$) at the other end of the jig along the circumferential surface of the lower head formation member 230.

Figure 9:
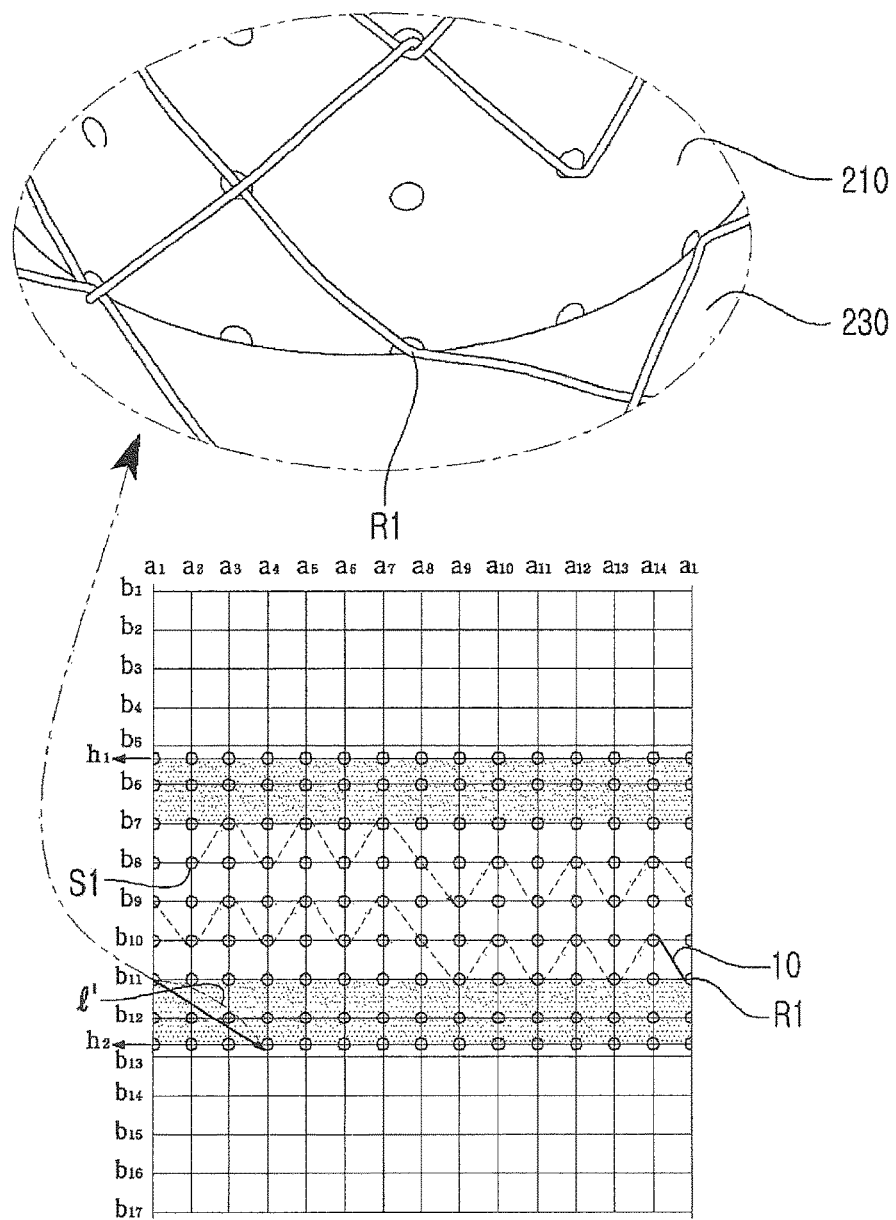
FIGS. 9 to 11 are development views illustrating a lower first head formation step according to the present invention.

In this process, first, there is performed a first lower part bending step of bending the first wire 10 at a first bending point R1 ($a_1/b_{11}$), reached by moving the first wire 10 from the first point F4 along a downward diagonal line of tangent lines, which the lower head formation member 230 forms with the jig 210, by l (the distance of a diagonal line extending by one interval between the length division lines for one interval between the circumference division lines), to come into contact with a lower bent portion 231 forming the ring-shaped bottom surface of the lower head formation member 230, as shown in FIG. 9.

Figure 10:
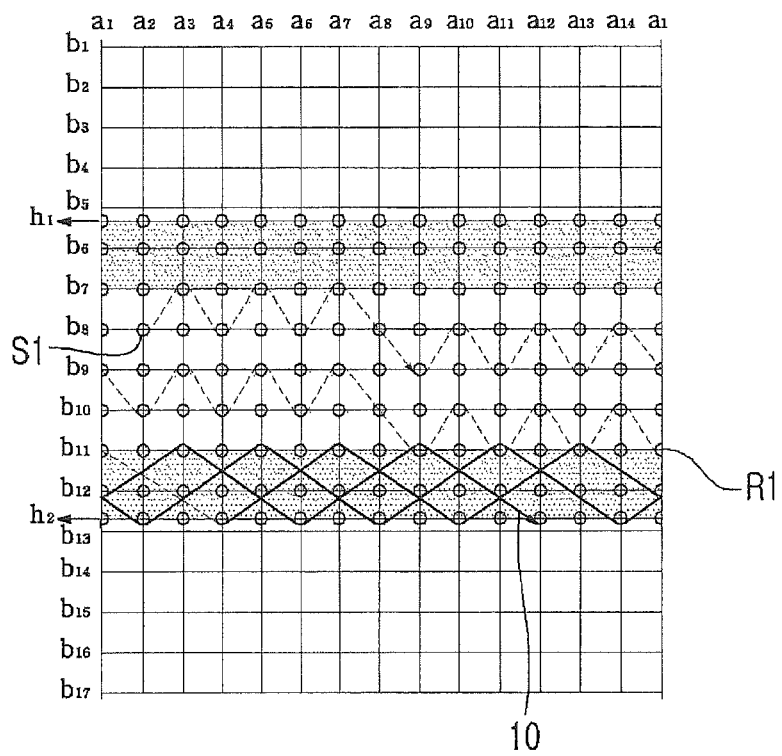

Thereafter, there is performed a lower head formation step of repeating a zigzag bent pattern formed by moving the first wire 10 bent from the first bending point R1 along a downward diagonal line by l' (a distance over which movement is performed from the first bending point R1 to the location point $a_4/h_2$, which corresponds to a circumference division line $a_4$ corresponding to a location that is shifted by three intervals based on the circumference division line $a_1$ of the first bending point R1, among location points on the head length division line $h_2$ set within the lower head formation member 230) along the circumferential surface of the lower curved portion 232 formed to extend in the shape in which the diameter of the lower curved portion 232 is increased from the lower bent portion 231 and is then decreased, and then moving the first wire 10 from the location point $a_4/h_2$ along an upward diagonal line by l' along the circumferential surface of the lower curved portion 232, thereby returning to the first bending point R1, as shown in FIG. 10.

Figure 11:
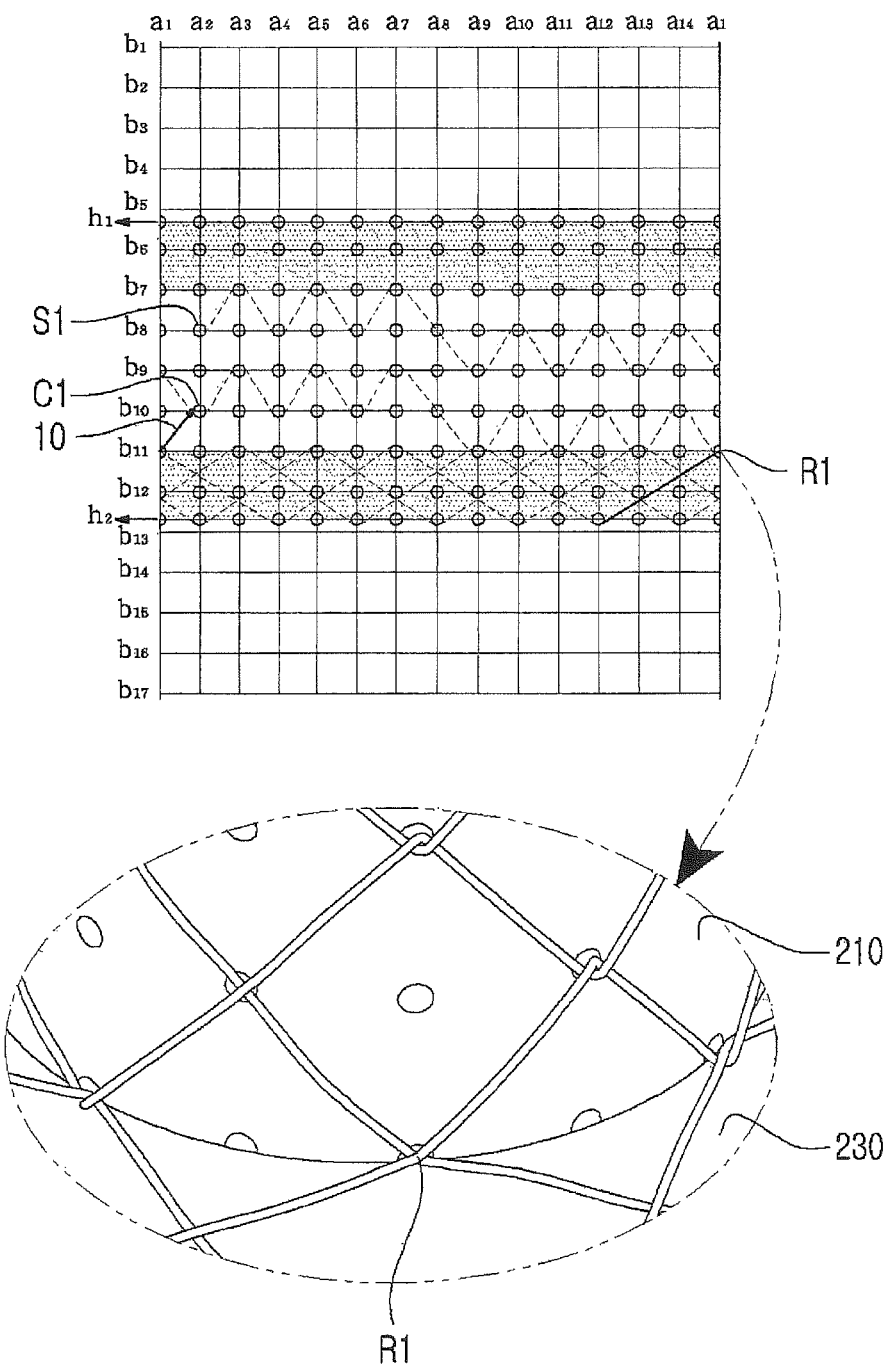

Finally, there is performed a second lower part bending step of bending the first wire 10, located at the first bending point R1, to come into contact with the circumferential surface of the jig 210 and then locating the first wire 10 at the first change point C1 by moving the first wire 10 from the first bending point R1 along an upward diagonal line by l, as shown in FIG. 11, thereby ending the lower first head formation step S200.

(3) First Wire Raising Step <S300>

Figure 12:
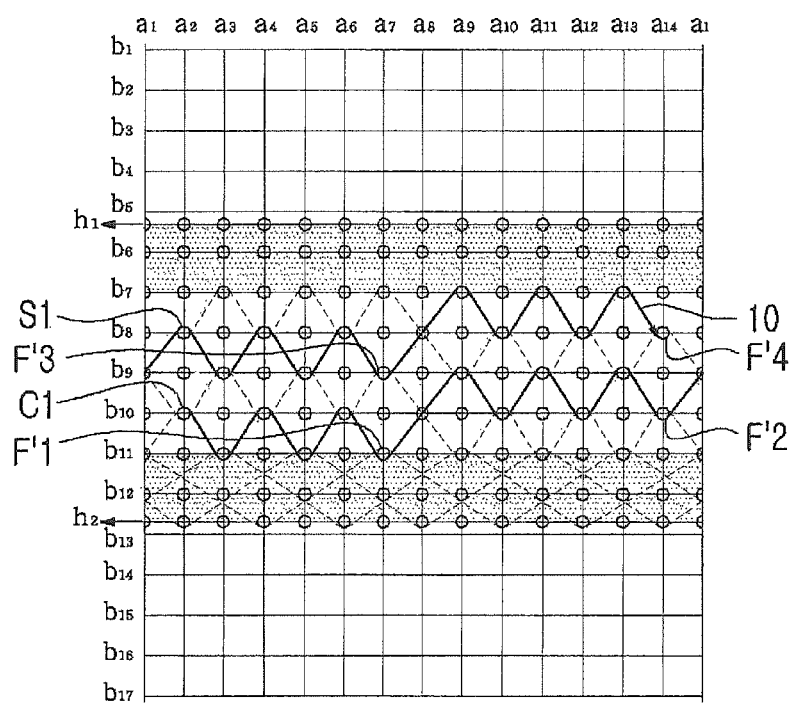
FIG. 12 is a development view illustrating a first wire raising step according to the present invention.

At the present step, as shown in FIG. 12, the first wire 10 is bent and moved from the first change point C1 at the other end of the jig to a second point F'4 ($a_{14}/b_8$) at the one end of the jig in a zigzag form.

As shown in FIG. 12, this process includes: a second zigzag movement step of repeating a zigzag bent pattern formed by moving the first wire 10 from the change point C1 along a downward diagonal line by l (the distance of a diagonal line extending by one interval between the length division lines for one interval between the circumference division lines) and then moving the first wire 10 from the location point $a_3/b_{11}$ along an upward diagonal line by l; and a second spacing step of spacing a location point from a portion formed at the zigzag movement step by moving the first wire 10 from the end point F'1 ($a_7/b_{11}$) of the second zigzag movement step along an upward diagonal line by 2l.

The second zigzag movement step and the second spacing step are alternately performed. That is, the second zigzag movement step and the second spacing step continue to be performed, as shown in FIG. 12. The first wire raising step S300 ends at the end point F'4 ($a_{14}/b_8$) of a specific second zigzag movement step.

As a result, a second point, which is the last location point of the first wire raising step S300 and which is the starting location point of the first head formation step 5400, corresponds to the last end point F'4 of many end points F'1, F'2, F'3 and F'4 formed in the process in which the second zigzag movement step and the second spacing step are alternately performed. The second point F'4 is located on the same length division line as the first starting point S1, and is located on the same circumference division line as an even-numbered end point F'2 of many end points F'1, F'2, F'3 an F'4 formed in the process in which the second zigzag movement step and the second spacing step are alternately performed.

(4) Upper First Head Formation Step <S400>

At the present step, there is performed an upper first head formation step of forming a part of the upper head 120 by repeating a pattern of bending the first wire 10 in a zigzag form from the second point F'4, located after a part of the stent body 110 has been formed during the raising of the first wire 10 via step S300, to the first starting point S1 at the one end of the jig along the circumferential surface of the upper head formation member 220.

Figure 13:
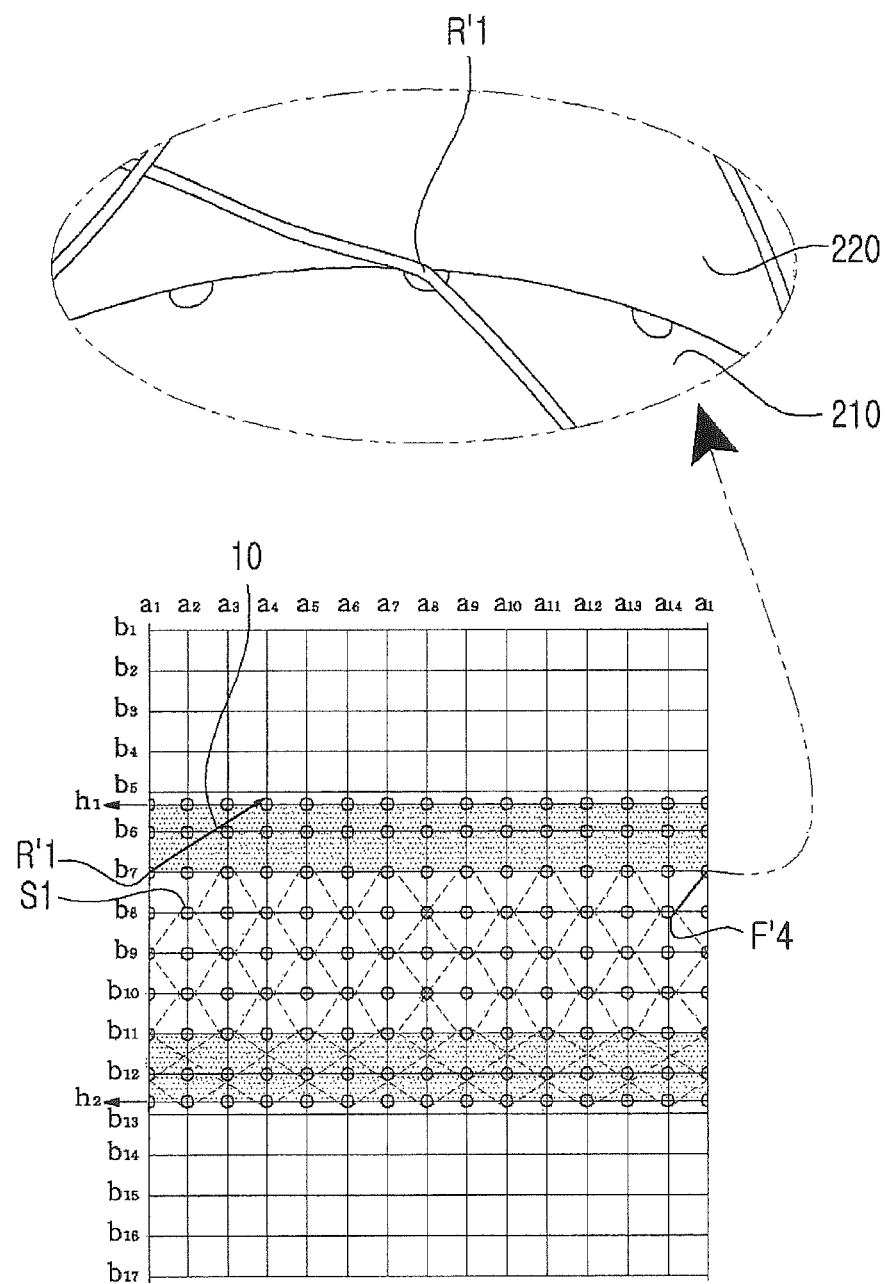
FIGS. 13 to 15 are development views illustrating an upper first head formation step according to the present invention.

In this process, first, there is performed a first upper part bending step of bending the first wire 10 at a second bending point R'1 ($a_1/b_7$), reached by moving the first wire 10 from the second point F'4 along an upward diagonal line of tangent lines, which the upper head formation member 220 forms with the jig 210, by l (the distance of a diagonal line extending by one interval between the length division lines for one interval between the circumference division lines), to come into contact with an upper bent portion 221 forming the ring-shaped bottom surface of the upper head formation member 230, as shown in FIG. 13.

Figure 14:
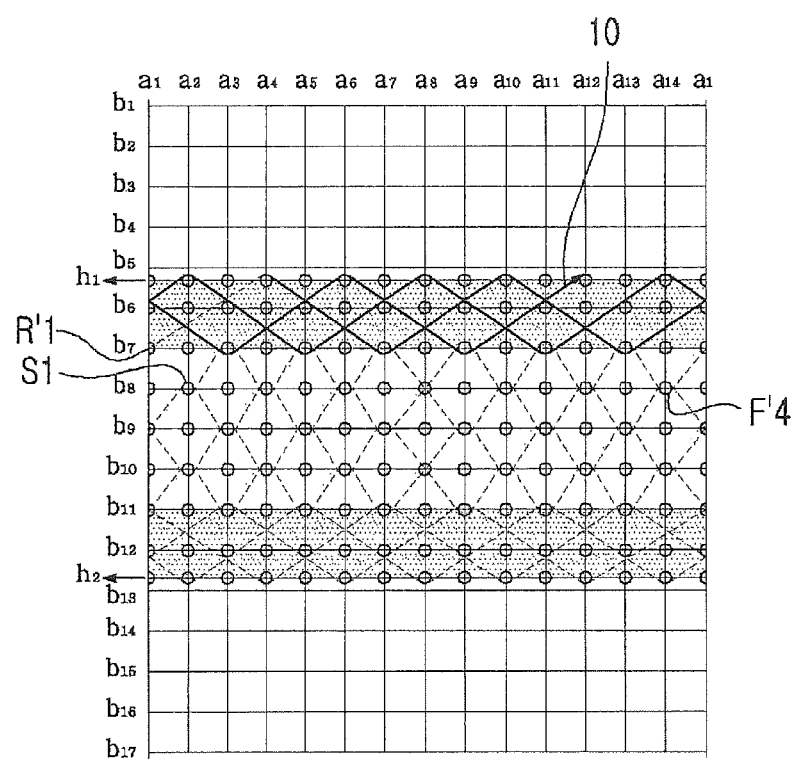

Thereafter, there is performed an upper head formation step of repeating a zigzag bent pattern formed by moving the first wire 10 bent from the second bending point R'1 along an upward diagonal line by l' (a distance over which movement is performed from the second bending point R'1 to the location point $a_4/h_1$, which corresponds to a circumference division line $a_4$ corresponding to a location point that is shifted by three intervals based on the circumference division line $a_1$ of the second bending point R'1, among location points on the head length division line $h_1$ set within the upper head formation member 220) along the circumferential surface of the upper curved portion 222 formed to extend in the shape in which the diameter is increased from the upper bent portion 221 and is then decreased, and then moving the first wire 10 from the location point $a_4/h_1$ along an upward diagonal line by l' along the circumferential surface of the upper curved portion 222, thereby returning to the second bending point R'1, as shown in FIG. 14.

Figure 15:
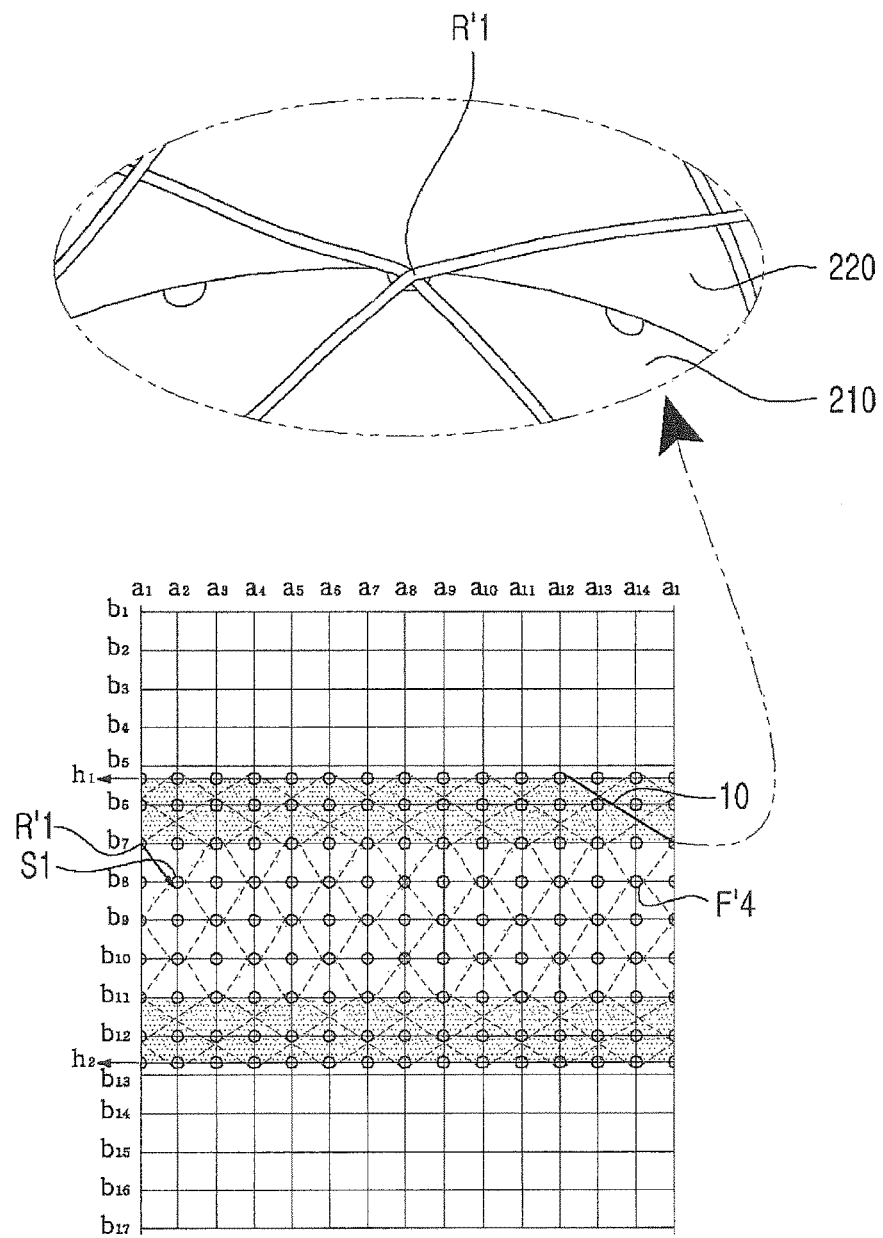
Figure 16:
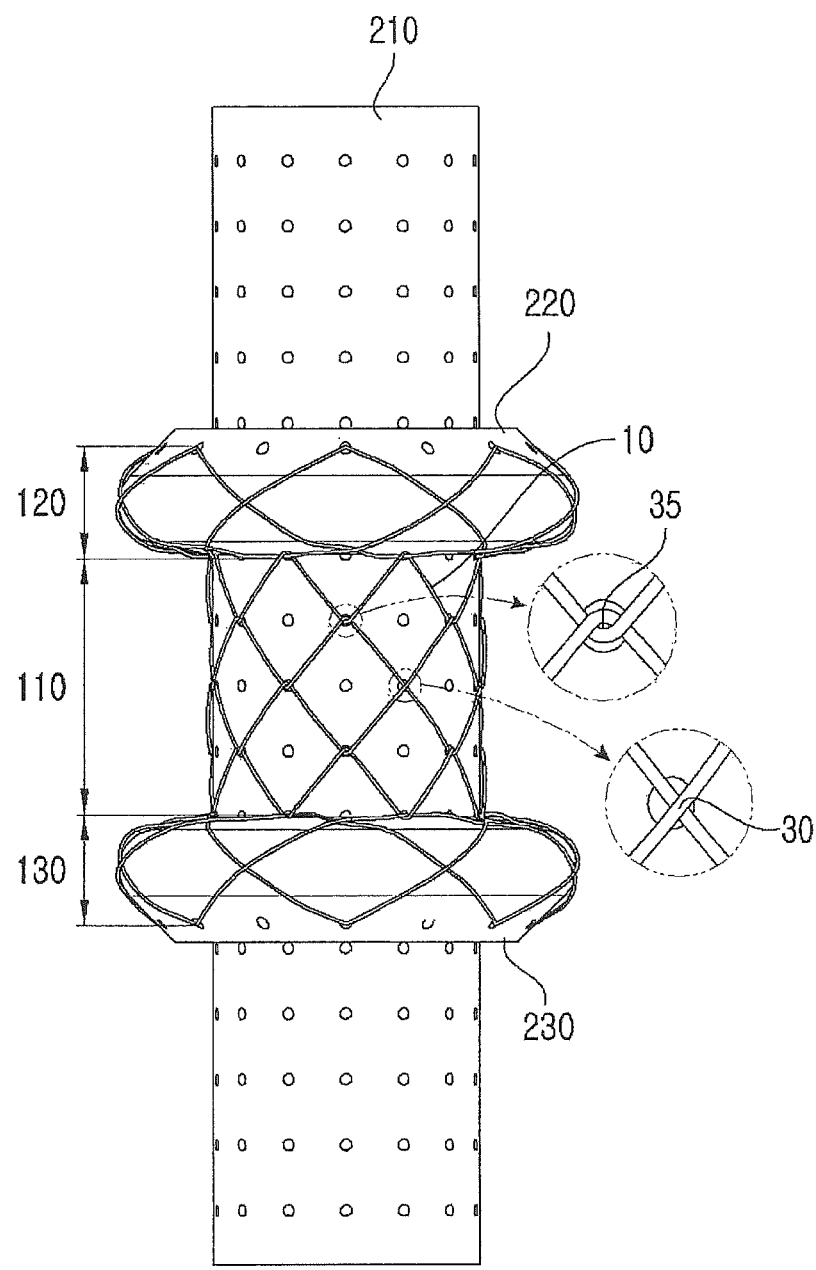
FIG. 16 is a perspective view showing the overall intersecting and bending states of a first wire on the connection stent manufacturing apparatus according to the present invention.

Finally, there is performed a second upper part bending step of bending the first wire 10, located at the second bending point R'1, to come into contact with the circumferential surface of the jig 210 and then locating the first wire 10 at the first starting point S1 by moving the first wire 10 from the second bending point R'1 along a downward diagonal line by l, as shown in FIG. 15, thereby ending the upper first head formation step S400.

The first wire 10 having returned to the first starting point S1 as described above is connected via welding or the like as a finishing process, as shown in FIG. 15, thereby forming the internal structure of the part of the connection stent 100.

In this case, in order to provide structural stability and sufficient expansion capability to the connection stent 100 formed via the above-described process, another second wire 20 is woven based on a different second starting point S2 ($a_3/b_8$) in the same manner, thereby manufacturing a connection stent 100 having a reinforced shape. A detailed method related to this will be described as follows.

A method of further manufacturing the connection stent 100 using the second wire 20 according to the present invention will be described with a focus on differences with the method of manufacturing the connection stent 100 using the first wire 10. Redundant descriptions will be abridged and omitted.

(5) Second Wire Lowering Step <S500>

Figure 17:
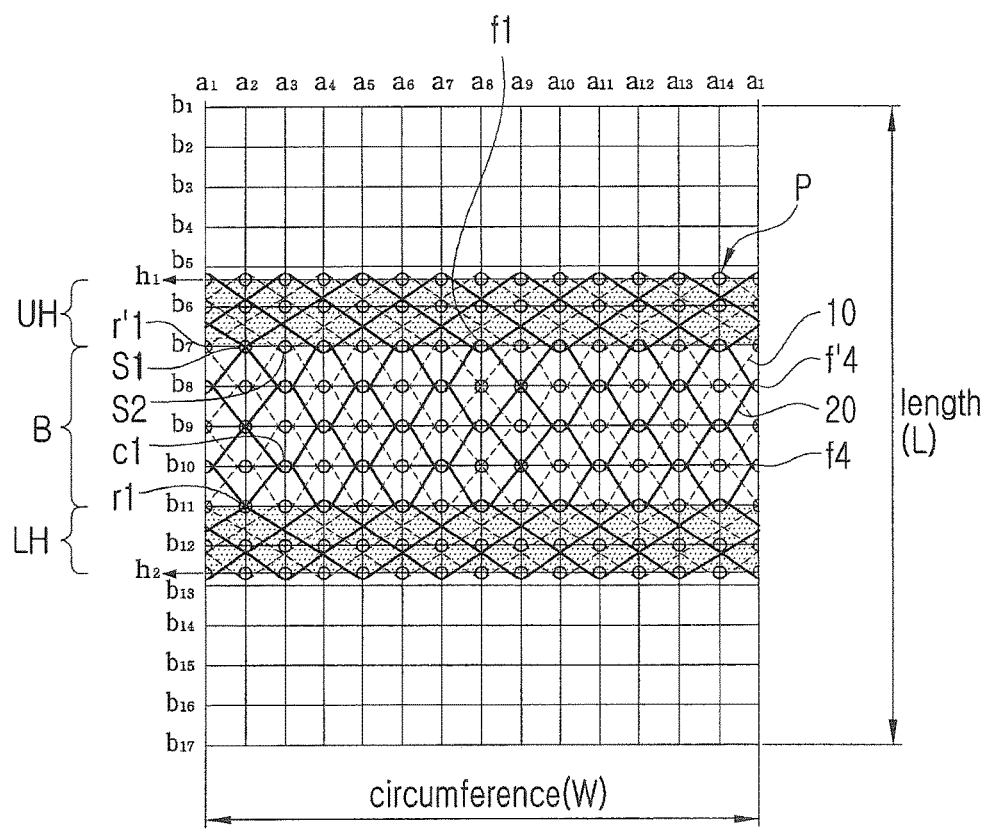
FIG. 17 is a development view showing the overall intersecting and bending states of a second wire according to the present invention.

At the present step, as shown in FIG. 17, the second wire 20 is bent and moved in a zigzag form from the second starting point S2 ($a_3/b_8$) at the one end of the jig to a third point f4 ($a_1/b_{10}$) at the other end of the jig.

In this case, the second starting point S2 is located to be spaced apart by a predetermined interval based on the circumference division lines, on an identical length division line on which the first starting point S1 is located. More specifically, the second starting point S2 preferably corresponds to a location point, which is shifted in a circumferential direction by an odd number of circumference division lines, on the identical length division line on which the first starting point S1 is located.

In this case, since a description of the methodological feature in which a part of the body 110 is formed by alternately performing a third zigzag movement step and a third spacing step within the second wire lowering step S500 corresponds to the description of the methodological feature of the first wire lowering step S100 using the first wire 10 according to the present invention in the same manner, a detailed description thereof is omitted.

(6) Lower Second Head Formation Step <S600>

At the present step, as shown in FIG. 17, there is performed a lower second head formation step of forming a part of the lower head 130 by repeating a pattern of bending the second wire 20 in a zigzag form from the third point f4, reached after the part of the stent body 110 has been formed during the lowering of the second wire 20 via step S500, to the second change point c1 ($a_3/b_{10}$) at the other end of the jig along the circumferential surface of the lower head formation member 230.

In this case, since a description of the methodological feature of the lower second head formation step S600 in which a part of the lower head 130 is formed by bending the second wire 20 and causing the second wire 20 to intersect in a zigzag form using the lower head formation member 230 corresponds to the description of the methodological feature of the lower first head formation step S200 using the first wire 10 according to the present invention, a detailed description thereof is omitted.

(7) Second Wire Raising Step <S700>

At the present step, as shown in FIG. 17, the second wire 20 is bent and moved from the second change point c1, reached via step S600, at the other end of the jig to a fourth point f'4 ($a_1/b_8$) at the one end of the jig in a zigzag form.

In this case, since a description of the methodological feature in which a part of the body 110 is formed by alternately performing a fourth zigzag movement step and a fourth spacing step within the second wire raising step S700 corresponds to the description of the methodological feature of the first wire raising step S300 using the first wire 10 according to the present invention in the same manner, a detailed description thereof is omitted.

(8) Upper Second Head Formation Step <S800>

At the present step, as shown in FIG. 17, there is performed an upper second head formation step of forming a part of the upper head 120 by repeating a pattern of bending the second wire 20 in a zigzag form from the fourth point f'4, reached after a part of the stent body 110 has been formed during the raising of the second wire 20 via step S700, to the second starting point S2 at the one end of the jig along the circumferential surface of the upper head formation member 220.

In this case, since a description of the methodological feature of the upper second head formation step S800 in which a part of the upper head 120 is formed by bending the second wire 20 and causing the second wire 20 to intersect in a zigzag form using the upper head formation member 220 corresponds to the description of the methodological feature of the upper first head formation step S400 using the first wire 10 according to the present invention, a detailed description thereof is omitted.

The second wire 20 having returned to the second starting point S2 as described above is connected via welding or the like as a finishing process, as shown in FIG. 17, thereby forming the external structure of the part of the connection stent 100.

Figure 18:
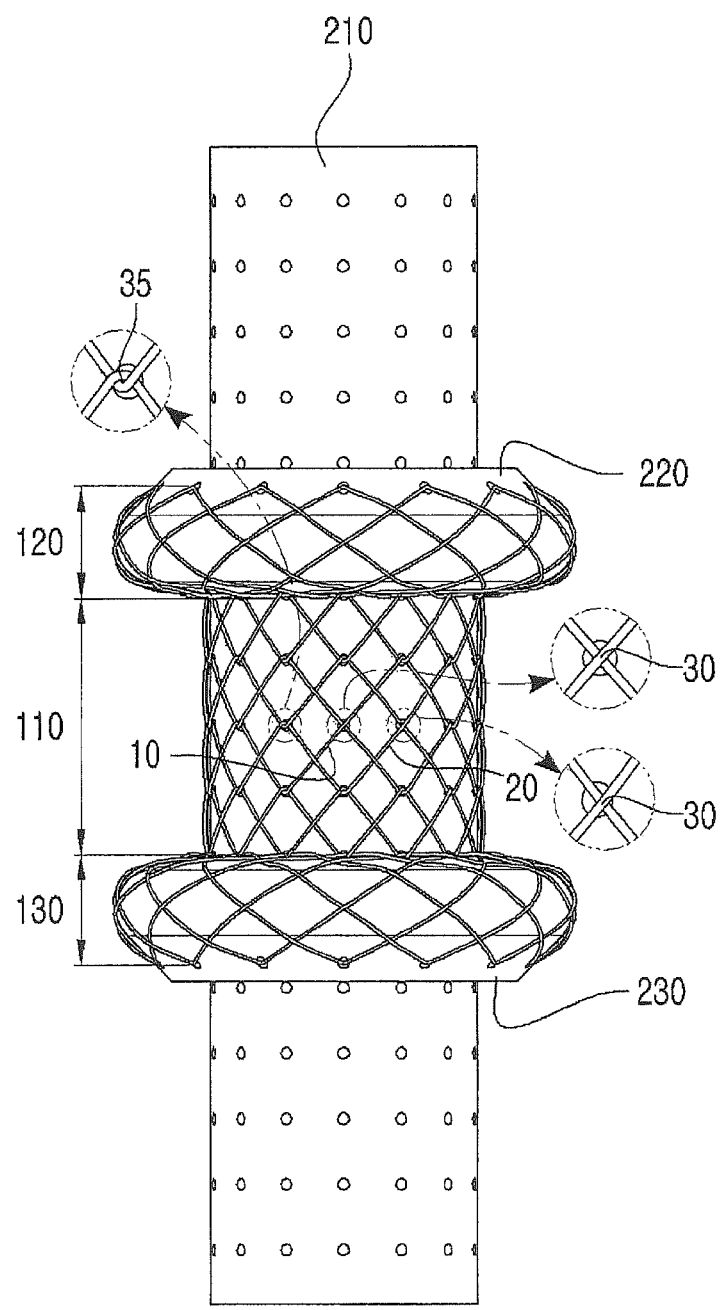
FIG. 18 is a perspective view showing the overall intersecting and bending states of the first wire and the second wire on the connection stent manufacturing apparatus according to the present invention.
Figure 19:
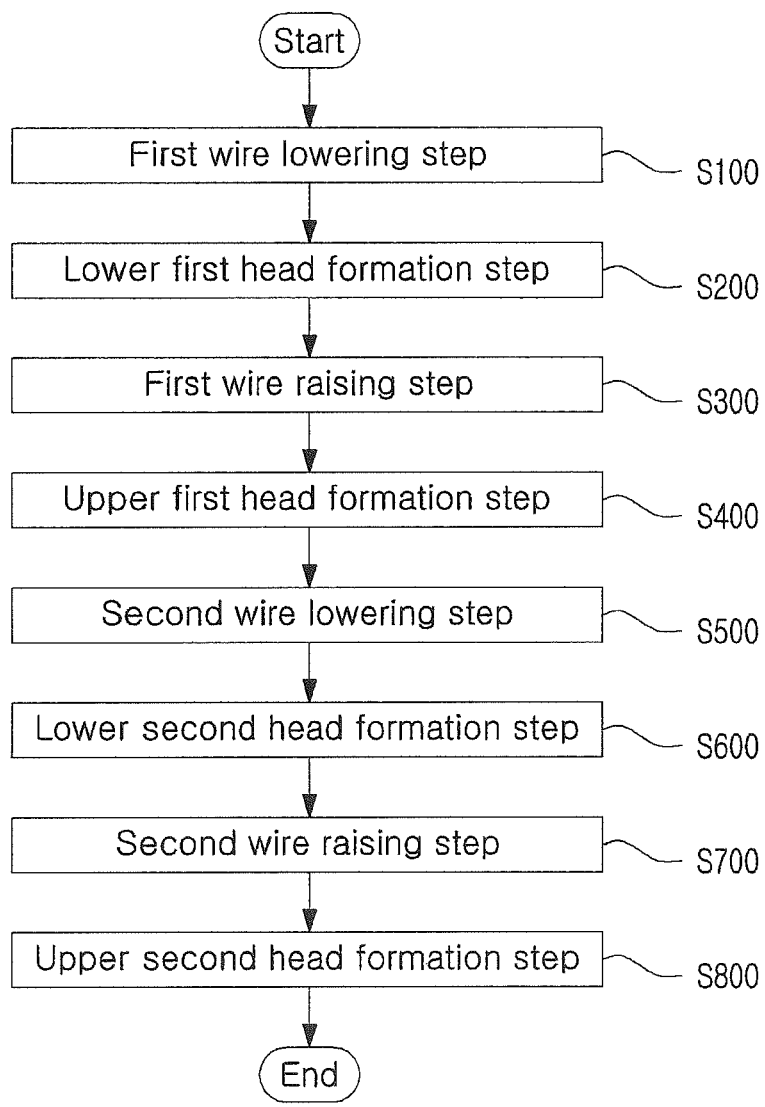
FIG. 19 is a flowchart showing a method of manufacturing a stent according to the present invention.

Furthermore, the internal structure formed by the first wire 10 and the external structure formed by the second wire 20 constitute a single overall connection stent 100 as a result, as shown in FIGS. 18 and 1.

3. Description of Features of Manufactured Stent

In the case of the connection stent 100 manufactured by the method of manufacturing a stent according to the present invention, a structure is formed through intersection via the described method, and thus areas constituting the components of the connection stent 100 have individual structural features.

More specifically, as shown in FIGS. 17 and 18, in the body 110 of the connection stent 100, the intersections of the wires located on specific circumference division lines $a_1$, $a_2$, $a_8$ and $a_9$ form intersections 30 without merging, while the intersections of the wires on the remaining circumference division lines are in a form in which the wires are hooked around both sides of the protruding pins P, thereby forming ring-shaped portions 35.

In this case, the wires intersect each other in a form in which the wires are hooked around each other on the remaining portions, exclusive of the specific circumference division lines $a_1$, $a_2$, $a_8$ and $a_9$, and empty portions are formed at the centers of the intersections by the protruding pins P, thereby forming the ring-shaped portions 35, as shown in the enlarged view of FIG. 18. These ring-shaped portions 35 provide spaces sufficient for changes in the shapes of cells in the case where the overall structure changes when the body 110, configured to connect heterogeneous tissues and form a bypass, is placed.

Furthermore, when a hollow cylindrical stent is implemented by connecting both ends of the connection stent 100 in the development view shown in FIG. 17, circumference division lines $a_1$ and $a_8$ face each other and circumference division lines $a_2$ and $a_9$ face each other. The intersections of the wires on the two pairs of the facing circumference division lines $a_1$ and $a_8$, and $a_2$ and $a_9$ form intersections 30. The implemented stent has sufficient variability so that it can be placed between heterogeneous tissues in a human body and then can form a bypass in accordance with the individual shapes of the tissues, and provides sufficient expansion capability to maintain a predetermined diameter for a prolonged period after the stent has been expanded.

In other words, the body 110 of the connection stent 100 manufactured by the manufacturing method according to the present invention appropriately forms a bypass between heterogeneous tissues based on the high-level flexibility thereof. The body 110 of the connection stent 100 exhibits axial force, acting in the axial direction of the stent, close to 0, and also exhibits high-level radial force acting to expand the stent outward. Accordingly, excellent durability attributable to the low fatigue of the wires can be achieved, and thus an inner cavity can be ensured inside a constricted region and an expanded state can be maintained for a prolonged period after the placement of the stent.

Additionally, the upper and lower heads 120 and 130 having the ring-shaped raised walls 121 and 131 and the curved head appearances 122 and 132 are formed via the upper head formation member 220 and the lower head formation member 230, and thus advantages can be achieved in that the upper and lower heads 120 and 130 disposed inside heterogeneous tissues, respectively, can ensure sufficient separation prevention capability and the degree of damage to the tissues that may occur when the wire constituting the head portions comes into contact with the inner surfaces of the tissues can be reduced.

The embodiments disclosed in the present invention are not intended to limit the technical spirit of the present invention, but are intended to illustrate the technical spirit of the present invention. The scope of the technical spirit of the present invention is not limited by the embodiments. The range of protection of the present invention should be based on the attached claims. All technical spirits that fall within a range equivalent to the claims should be interpreted as being included in the range of rights of the present invention.

DESCRIPTION OF REFERENCE SYMBOLS

100: connection stent
110: body
120: upper head
121: first portion
122: second portion
123: third portion
130: lower head
131: fourth portion
132: fifth portion
133: sixth portion
200: connection stent manufacturing apparatus
210: jig
220: upper head formation member
221: upper bent portion
222: upper curved portion
230: lower head formation member
231: lower bent portion
232: lower curved portion
P: protruding pin
10: first wire
20: second wire
30: intersection portion
35: ring-shaped portion

The invention claimed is:

1. A connection stent, comprising:
a body configured to form a plurality of cells through intersections of wires, and provided in a hollow cylindrical shape;
an upper head formed to extend from one end of the body to have a diameter larger than a diameter of the body; and
a lower head formed to extend from a remaining end of the body to have a diameter larger than the diameter of the body;
wherein the upper head and the lower head are respectively placed to come into contact with insides of heterogeneous tissues,
wherein the upper head comprises:
a first portion bent and formed to extend from the one end of the body toward directions away from an outer circumference of the body;

a second portion formed to extend from the first portion toward directions away from the one end of the body in a shape in which a diameter thereof is increased; and a third portion formed to extend from the second portion toward directions away from the one end of the body in a shape in which a diameter is decreased until it reaches a terminal end of the third portion, the terminal end of the third portion being perpendicular to a central axis of the body, wherein the lower head comprises:

a fourth portion bent and formed to extend from the remaining end of the body toward directions away from the outer circumference of the body;

a fifth portion formed to extend from the fourth portion toward directions away from the remaining end of the body in a shape in which a diameter thereof is increased; and a sixth portion formed to extend from the fifth portion toward directions away from the remaining end of the body in a shape in which a diameter is decreased until it reaches a terminal end of the sixth portion, the terminal end of the sixth portion being perpendicular to a central axis of the body, wherein the first portion is bent from the one end of the body toward directions away from the outer circumference of the body at an angle ranging from 85° to less than 90° with respect to the central axis of the body, wherein the fourth portion is bent from the remaining end of the body toward directions away from the outer circumference of the body at an angle ranging from 85° to less than 90° with respect to the central axis of the body, wherein a diameter of the terminal end of the third portion is larger than the diameter of the body, and a diameter of the terminal end of the sixth portion is larger than the diameter of the body, wherein the decrease in the diameter of the third portion in directions away from the second portion is more gradual than the increase in a diameter of the first portion in directions towards the second portion, and the decrease in the diameter of the sixth portion in directions away from the fifth portion is more gradual than the increase in a diameter of the fourth portion in directions towards the fifth portion, wherein the diameter of the first portion is increased from the diameter of the body, and the diameter of the fourth portion is increased from the diameter of the body so that a smallest diameter of the first and fourth portions is equal to the diameter of the body, wherein a smallest diameter of the third portion is equal to the diameter of the terminal end of the third portion, and a smallest diameter of the sixth portion is equal to the diameter of the terminal end of the sixth portion.

2. The connection stent of claim 1, wherein the first portion and the fourth portion are bent toward directions away from the outer circumference of the body at an identical angle with respect to the central axis of the body, and are provided so as to be opposite to each other.

3. The connection stent of claim 1, wherein the intersections of wires include at least one intersection where one wire hooks with the other wire so that the at least one intersection forms a ring-shaped portion.

4. The connection stent of claim 3, wherein the intersections of wires are arranged in a pattern in which the wires run vertically and are bent into a zig-zag pattern so that each "zig" hooks with the wire immediately on one side and each "zag" with the wire immediately on the other.

* * * * *